United States Patent
Tongiani et al.

(10) Patent No.: US 10,507,173 B2
(45) Date of Patent: Dec. 17, 2019

(54) DEODORANT COMPOSITION COMPRISING A MIXTURE OF ALPHA, BETA, AND GAMMA CYCLODEXTRIN

(71) Applicant: AZIENDE CHIMICHE RIUNITE ANGELINI FRANCESCO A.C.R.A.F. S.p.A., Rome (IT)

(72) Inventors: Serena Tongiani, Grottaferrata (IT); Lorella Ragni, Chiaravalle (IT); Daniela Donelli, Ancona (IT)

(73) Assignee: AZIENDE CHIMICHE RIUNITE ANGELINI FRANCESCO A.C.R.A.F. S.p.A., Rome (IT)

( * ) Notice: Subject to any disclaimer, the term of this patent is extended or adjusted under 35 U.S.C. 154(b) by 28 days.

(21) Appl. No.: 15/736,639

(22) PCT Filed: Jun. 21, 2016

(86) PCT No.: PCT/EP2016/064250
§ 371 (c)(1),
(2) Date: Dec. 14, 2017

(87) PCT Pub. No.: WO2016/207133
PCT Pub. Date: Dec. 29, 2016

(65) Prior Publication Data
US 2018/0185261 A1  Jul. 5, 2018

(30) Foreign Application Priority Data

Jun. 25, 2015 (EP) .................................. 15173747

(51) Int. Cl.
*A61K 8/73* (2006.01)
*A61Q 15/00* (2006.01)

(52) U.S. Cl.
CPC .............. *A61K 8/738* (2013.01); *A61Q 15/00* (2013.01); *A61K 2800/5922* (2013.01)

(58) Field of Classification Search
CPC .............................. A61K 8/738; A61Q 15/00
See application file for complete search history.

(56) References Cited

U.S. PATENT DOCUMENTS

| 5,733,272 A | 3/1998 | Brunner et al. | |
|---|---|---|---|
| 5,858,335 A | 1/1999 | Lucas et al. | |
| 6,123,932 A | 9/2000 | Guskey et al. | |
| 6,344,218 B1* | 2/2002 | Dodd | A61K 8/0208 424/405 |
| 2003/0191034 A1* | 10/2003 | Woo | A61L 9/01 510/101 |
| 2012/0083467 A1* | 4/2012 | Ayala | A61K 8/731 514/58 |

FOREIGN PATENT DOCUMENTS

| EP | 0 691 856 B1 | 6/2002 | |
|---|---|---|---|
| EP | 0 939 614 B1 | 12/2002 | |
| EP | 1 006 993 B1 | 10/2004 | |
| EP | 0 988 364 B1 | 8/2005 | |
| EP | 1 185 238 B1 | 10/2005 | |
| EP | 1 176 944 B1 | 9/2006 | |
| WO | WO-2008103657 A2 * | 8/2008 | ............... B29B 9/06 |

OTHER PUBLICATIONS

International Search Report dated Aug. 16, 2016 in PCT/EP2016/064250 filed Jun. 21, 2016, 4 pages.
Susanna Mitro, et al., "The Smell of Age: Perception and Discrimination of Body Odors of Different Ages", PLOS ONE, vol. 7, No. 5, E38110, May 2012, XP002743668, 1-7 pages.

* cited by examiner

*Primary Examiner* — Gina C Justice
(74) *Attorney, Agent, or Firm* — Oblon, McClelland, Maier & Neustadt, L.L.P.

(57) ABSTRACT

This invention relates to an odour-absorbing composition comprising a mixture of α-, β-, and γ-cyclodextrins, wherein the amount of one of said α-, β-, and γ-cyclodextrins is equal to or higher than the total amount of the other two cyclodextrins.

7 Claims, 3 Drawing Sheets

DEODORANT COMPOSITION COMPRISING A MIXTURE OF ALPHA, BETA, AND GAMMA CYCLODEXTRIN

FIELD OF THE INVENTION

This invention relates to a deodorant composition comprising a mixture of α, β, and γ cyclodextrin. More in particular, this invention relates to a deodorant composition comprising mixtures of α, β, and γ cyclodextrin in a specific ratio for controlling malodour associated with the perspiration of humans of different age and sex.

STATE OF THE ART

Body odour is most commonly caused by fatty acids on skin and by malodours from microbial sources. The human skin is naturally populated with numerous microorganisms which are nourished by various skin secreted substances (eccrine and apocrine sweat, and sebum), skin cell debris, breakdown products of the skin and the organisms themselves. These unpleasant body odours are mainly organic molecules which have different structures and functional groups, such as amines, acids, alcohols, aldehydes, ketones, phenols, indoles, aromatics, polyaromatics, and so on. They can also be made up of sulphur containing functional groups, such as, thiol, mercaptan, sulfide and/or disulfide groups.

Furthermore, daily contact with substances which leave unpleasant odours on an individual's body and hair is almost unavoidable. Foods such as fish, onions, garlic or other spices, cooking odours, smoke, tobacco, and gasoline are just a few of the common environmental sources of malodours in daily life.

Numerous attempts have been made to conceal unpleasant odours through the use of deodorizing compositions. These compositions typically rely on the presence of antimicrobial agents and/or fragrances to control or mask malodours.

Other attempts at controlling malodours resulting from perspiration include the use of odour absorbers such as activated charcoal and zeolites.

Another attempt at controlling malodours resulting from perspiration include the use of cyclodextrin odour controlling agents. The use of cyclodextrins to absorb odours including body odours such as perspiration malodours, is well known. Solid and liquid deodorant composition comprising cyclodextrins are disclosed, for example, in EP0691856, EP0939614, EP988364, EP1006993, EP1176944 and EP1185238.

Recent studies have shown that the body odour carries age-related and gender-related information. While it is known that the chemical composition of body odour changes with age in many animals such as mice, rabbits and some primates, in the case of humans, there have been few studies focusing on the change in body odour with age or gender.

However, it is possible to identify three stages of life, from the point of view of body odour, namely, youth, adulthood and old age. In adulthood it is possible to make a further distinction based on sex. Therefore, humans can be classified in four categories based on differences in body odour: teenagers, the elderly, women and men.

The generation of malodour on various sites of the human body, for example, foot, mouth, or armpit is mainly caused by microbial transformation of odourless natural secretions into volatile odorous molecules. In humans, sebaceous, eccrine and apocrine sweat glands provide an important source of nutrients for bacterial (Corynebacteria and Staphylococci species) growth The major and specific constituents of human sweat are two volatile steroids, androstenone in men and androstenol in women, both formed from androsterone, a volatile fatty acid, 3-hydroxy-3-methylhexanoic acid (HMHA), subsequently transformed in 3-methyl-2-hexanoic acid (MHA), found in men and women sweat even if prevalent in men, and a sulphanylalkanol, 3-methyl-3-sulfanylhexan-1-ol (MSH), prevalent in women.

In teenagers, because of hormonal imbalances, the intensity of axillary malodour increases perceivably during the puberty as apocrine sweat glands do not became active until this development stage. Teenagers experience mental stress in various parts of life like during school exams, job interviews or first dates. Emotional sweating is a physical reaction to emotive stimuli like stress, anxiety or mental tension that can occur over the whole body surface but is most prominent on palms, soles and in the armpits. Interestingly, although emotional sweating on palms and soles already occurs in infants, emotional sweating in the axillary region does not occur until puberty. In the axillary region, eccrine sweat glands secrete a watery fluid while apocrine sweat glands secrete a variety of non-smelling odorant precursors, that are transformed to volatile odoriferous substances, by bacterial enzymes on the skin surface. Because during stressful situations both types of sweat glands become activated, emotional sweating is characterized by enhanced sweat secretion (osmidrosis) along with a strong axillary odour, making it very unpleasant. In particular, the concentration of dihydrotestosterone (17β-Hydroxy-5α-androstan-3-one or DHT) and testosterone (17β-Hydroxy-4-androsten-3-one) has been found to be high in the sweat of teenagers.

In older people, i.e., people over 50 years old, the decreased androgen production may contribute to a change in skin odour as the metabolic activity of apocrine and sebaceous glands is under control of androgenic hormones. The sebaceous gland is formed over much of the skin's surface and secretes a complex mixture of lipids (sebum) and fatty acids, both important precursor to human dermal body odor. Hexanal, octenal and nonenal are formed through the oxidative degradation of unsaturated fatty acids in skin surface. The 2-nonenal, an unsaturated aldehyde with an unpleasant greasy and grassy odour, was detected only in older subject and not in subjects aged under 40. The corresponding saturated aldehyde nonanal also was more abundant in older subjects and was found in both back and forearm.

SUMMARY OF THE INVENTION

After extensive investigation, the Applicant has surprisingly found that ternary mixtures of α-, β-, and γ-cyclodextrins with a specific weight ratio can provide better and different results in controlling and masking the body odours in teenagers, adult men and women, and older people.

The Applicant has found that ternary mixtures of α-, β-, and γ-cyclodextrins are more effective in older people when the amount of α-cyclodextrins is prevalent over the amount of β-, and γ-cyclodextrins, in particular when the weight ratio of α-, β-, and γ-cyclodextrins is about 2:1:1.

The Applicant has also found that ternary mixtures of α-, β-, and γ-cyclodextrins are more effective in adult men when the amount of β-cyclodextrins is prevalent over the amount of α-, and γ-cyclodextrins, in particular when the weight ratio of α-, β-, and γ-cyclodextrins is about 1:2:1.

The Applicant has also found that ternary mixtures of α-, β-, and γ-cyclodextrins are more effective in adult women when the amount of γ-cyclodextrins is prevalent over the amount of α-, and β-cyclodextrins, in particular when the weight ratio of α-, β-, and γ-cyclodextrins is about 1:1:2.

Finally, the Applicant has also found that ternary mixtures of α-, β-, and γ-cyclodextrins are more effective in teenagers when the amount of β-cyclodextrins is prevalent over the amount of α-cyclodextrins, which in turn is prevalent over the amount of γ-cyclodextrins, in particular when the weight ratio of α-, β-, and γ-cyclodextrins is about 1:1.5:0.5.

Thus, in a first aspect this invention relates to an odour-absorbing composition comprising a mixture of α-, β-, and γ-cyclodextrins, wherein the amount of one of said α-, β-, and γ-cyclodextrins is equal to or higher than the total amount of the other two cyclodextrins.

According to a first preferred embodiment, the present invention relates to an odour-absorbing composition comprising a mixture of α-, β-, and γ-cyclodextrins, wherein the amount of α-cyclodextrins is equal to or higher than the total amount of β-, and γ-cyclodextrins.

Advantageously, the present invention relates to an odour-absorbing composition comprising a mixture of α-, β-, and γ-cyclodextrins in a weight ratio of about 2:1:1.

According to a second preferred embodiment, the present invention relates to an odour-absorbing composition comprising a mixture of α-, β-, and γ-cyclodextrins, wherein the amount of β-cyclodextrins is equal to or higher than the total amount of α-, and γ-cyclodextrins.

Advantageously, the present invention relates to an odour-absorbing composition comprising a mixture of α-, β-, and γ-cyclodextrins in a weight ratio of about: 1:2:1.

According to a third preferred embodiment, the present invention relates to an odour-absorbing composition comprising a mixture of α-, β-, and γ-cyclodextrins, wherein the amount of γ-cyclodextrins is equal to or higher than the total amount of α-, and β-cyclodextrins.

Advantageously, the present invention relates to an odour-absorbing composition comprising a mixture of α-, β-, and γ-cyclodextrins in a weight ratio of about: 1:1:2.

According to a fourth preferred embodiment, the present invention relates to an odour-absorbing composition comprising a mixture of α-, β-, and γ-cyclodextrins, wherein the amount of β-cyclodextrins is equal to or higher than the total amount of α-, and γ-cyclodextrins, and the amount of α-cyclodextrins is higher than the amount of γ-cyclodextrins. Advantageously, the present invention relates to an odour-absorbing composition comprising a mixture of α-, β-, and γ-cyclodextrins in a weight ratio of about: 1:1.5:0.5.

DETAILED DESCRIPTION OF THE INVENTION

The present invention relates to an odour-absorbing composition comprising a mixture of α-, β-, and γ-cyclodextrins, wherein the amount of one of said α-, β-, and γ-cyclodextrins is equal to or higher than the total amount of the other two cyclodextrins.

As used herein, the term "cyclodextrin" includes any of the known cyclodextrins such as unsubstituted cyclodextrins containing from six to twelve glucose units, and/or their derivatives and/or mixtures thereof.

Preferred, the cyclodextrins used in the present invention are highly water-soluble α-cyclodextrin and/or derivatives thereof, β-cyclodextrin and/or derivatives thereof, and γ-gamma-cyclodextrin and/or derivatives thereof, and/or mixtures thereof.

The derivatives of cyclodextrin consist mainly of molecules wherein some of the OH groups are converted to OR groups, wherein R is an alkyl group having from 1 to 6 carbon atoms, preferably from 1 to 3 carbon atoms.

Highly water-soluble cyclodextrins are those having water solubility of at least about 10 g in 100 ml of water at room temperature, preferably at least about 20 g in 100 ml of water, more preferably at least about 25 g in 100 ml of water at room temperature.

The concentration of cyclodextrins in the odour-absorbing composition of the present invention can be from about 0.1% to about 5%, preferably from about 0.2% to about 4%, more preferably from about 0.3% to about 3%, most preferably from about 0.4% to about 2%, by weight, based on the total weight of the odour-absorbing composition.

Concentrated compositions can also be used. When a concentrated product is used, i.e., when the concentration of cyclodextrin used in the odour-absorbing composition of the present invention is from about 3% to about 5%, it is preferable to dilute the composition before applying to the skin in order to avoid tacky skin feel and/or an undesirable amount of residue. Preferably the cyclodextrin is diluted with about 50% to about 2000%, more preferably with about 60% to about 1000%, most preferably with about 75% to about 500%, by weight of the composition of water.

In a first preferred embodiment of the present invention, the odour-absorbing composition comprises an amount of α-cyclodextrins equal to or higher than the total amount of β-, and γ-cyclodextrins.

Preferably, the weight ratio of the amount of α-cyclodextrins, to the amount of β-, and γ-cyclodextrins ranges from 4:1 to 1:1, more preferably from 2:1 to 1:1.

Advantageously, the odour-absorbing composition comprises an amount of α-, β-, and γ-cyclodextrins in a weight ratio of about 2:1:1.

In a second preferred embodiment of the present invention, the odour-absorbing composition comprises an amount of β-cyclodextrins equal to or higher than the total amount of α-, and γ-cyclodextrins.

Preferably, the weight ratio of the amount of β-cyclodextrins, to the amount of α-, and γ-cyclodextrins ranges from 4:1 to 1:1, more preferably from 2:1 to 1:1.

Advantageously, the odour-absorbing composition comprises an amount of α-, β-, and γ-cyclodextrins in a weight ratio of about 1:2:1.

In a third preferred embodiment of the present invention, the odour-absorbing composition comprises an amount of γ-cyclodextrins equal to or higher than the total amount of α-, and β-cyclodextrins.

Preferably, the weight ratio of the amount of γ-cyclodextrins, to the amount of α-, and β-cyclodextrins ranges from 4:1 to 1:1, more preferably from 2:1 to 1:1.

Advantageously, the odour-absorbing composition comprises an amount of α-, β-, and γ-cyclodextrins in a weight ratio of about 1:1:2.

In a fourth preferred embodiment of the present invention, the odour-absorbing composition comprises an amount of β-cyclodextrins equal to or higher than the total amount of α-, and γ-cyclodextrins, and an amount of α-cyclodextrins higher than the amount of γ-cyclodextrins.

Preferably, the weight ratio of the amount of β-cyclodextrins, to the amount of α-, and γ-cyclodextrins ranges from 4:1 to 1:1, more preferably from 2:1 to 1:1, and the weight ratio of the amount of α-cyclodextrins to γ-cyclodextrins ranges from 4:1 to 1.5:1.

Advantageously, the odour-absorbing composition comprises an amount of α-, β-, and γ-cyclodextrins in a weight ratio of about: 1:1.5:0.5.

The complexation between cyclodextrin and odorous molecules occurs rapidly in the presence of water when the solubilized cyclodextrins are first applied to the skin. Additionally, cyclodextrins which dry on the skin surfaces will once again achieve enhanced absorption capabilities when rewetted with body fluids. This is convenient for the user because the cyclodextrins, while on dry skin, will not fill their cavities with other environmental odours which would otherwise render them less efficient for absorbing body odours. More particularly, upon solubilisation of the cyclodextrins by the body fluids, the isolated cavities become available to form inclusion complexes with the body odour molecules. Thus, ultimately, the availability of solubilized uncomplexed cyclodextrin is essential for an effective and efficient odour control performance.

The odour-absorbing composition of the present invention can contain a variety of other optional components suitable for rendering such compositions more cosmetically or aesthetically acceptable or to provide them with addition usage benefits. Such conventional optional ingredients are well-known to those skilled in the art. These include any cosmetically acceptable ingredients such as those found in the CTFA International Cosmetic Ingredient Dictionary and Handbook, 7th edition, edited by Wenninger and McEwen, (The Cosmetic, Toiletry, and Fragrance Association, Inc., Washington, D.C., 1997). As used herein "cosmetically acceptable" means a material (e. g., compound or composition) which is suitable for use in contact with skin, hair or other suitable substrate as defined hereinbelow.

Cosmetically acceptable ingredients useful in the present invention includes cosmetically acceptable carriers, volatile and non-volatile solvents, water, and other additional ingredients, such as surfactants, preservatives, absorbents, chelating agents, lubricants, moisturizers water repellents, antioxidants, UV absorbers, anti-irritants, vitamins, trace metals, anti-microbial agents, perfumes, dyes and colour ingredients, and/or structuring agents The expression "cosmetically acceptable carrier", as used herein, means one or more compatible solid or liquid fillers, diluents, extenders and the like, which are cosmetically acceptable as defined hereinabove. The term "compatible", as used herein, means that the components of the compositions of this invention are capable of being combined with the primary actives of the present invention, and with each other, in a manner such that there is no interaction which would substantially reduce the efficacy of the composition under ordinary use situations. The type of carrier utilized in the present invention depends on the type of product desired.

The compositions useful in the present invention may be a wide variety of product forms. These include, but are not limited to, lotions, creams, gels, sticks, sprays, ointments, pastes, mousses and cosmetics (e. g., solid, semi-solid, or liquid make-up, including foundations).

These product forms may comprise several types of carriers including, but not limited to, solutions, aerosols, emulsions (including oil-in-water or water-in-oil), gels, solids, and liposomes.

The compositions of the present invention may comprise water, in different amounts depending on the form of the composition. The amount of water, if present, can range from less than 1% to more than 99% by weight with respect to the weight of total composition.

Solid compositions, spray compositions, and water-in-oil creams usually comprise amounts of water lower than 10%, more preferably lower than 5% by weight with respect to the total weight of the composition. Roll-on compositions, aqueous compositions, and deodorant usually comprises amount of water of from about 15% to about 99%, more preferably from about 30% to about 90%, even more preferably about 50% to about 80%, by weight with respect to the total weight of the composition.

The compositions of the present invention may also comprise silicones. If present, the silicones will generally be at a level of from about 30% to about 85%, more preferably from about 40% to about 75%, even more preferably about 50% to about 65%, by weight with respect to the total weight of the composition. The silicones useful herein are preferably cyclic siloxanes such as octamethyl cyclotetrasiloxane, decamethylcyclopentasiloxane, and.

The silicones useful herein are preferably linear or cyclic silicones having from 2 to 7 silicone atoms, these silicones being optionally substituted with alkyl or alkoxy groups of 1 to 10 carbon atoms. Suitable silicones include dodecamethylcyclohexasiloxane, cyclopentasiloxane, decamethylcyclopentasiloxane, cyclotetrasiloxane, heptamethyloctyltrisiloxane, hexamethyldisiloxane, decamethyltetrasiloxane, dodeca-methylpentasiloxane octamethyltetrasiloxane and mixtures thereof.

The compositions of the present invention may comprise one or more volatile solvent. If present, the volatile solvent or mixture of solvents will generally be at a level of from about 10% to about 90%, more preferably from about 25% to about 75%, even more preferably about 35% to about 65%, by weight with respect to the total weight of the composition. The solvents useful herein are preferably organic volatile solvents.

As used herein, "volatile" refers to substances with a significant amount of vapour pressure under ambient conditions, as is understood by those in the art.

The volatile solvents for use herein will preferably have a vapour pressure of about 2 kPa or more, more preferably about 6 kPa or more, at 25° C. The volatile solvents for use herein will preferably have a boiling point under normal atmosphere (1 atm) of less than about 150° C., more preferably less than about 100° C., even more preferably less than about 90° C., even more preferably still less than about 80° C.

Preferably the volatile solvents for use herein will be relatively odourless and safe for use on human skin. Suitable volatile solvents include, but are not limited to $C_1$-$C_4$ alcohols, volatile silicones and mixtures thereof. Preferred volatile solvents are $C_1$-$C_4$ alcohols and mixtures thereof. More preferred for use herein is ethanol.

The compositions of the present invention may also comprise one or more non-volatile solvent. If present, the non-volatile solvent or mixture of solvents will generally be at a level of from about 1% to about 20%, more preferably from about 2% to about 10%, even more preferably from about 3% to about 5%, by weight with respect to the total weight of the composition. Suitable non-volatile solvents include, but are not limited to, benzyl benzoate, cetearyl alcohol, cetyl alcohol, diethyl phthalate, isopropyl myristate, dimethicone, caprylylmethicone, and mixtures thereof.

Several other additional ingredients can be present in the compositions of the present invention. These include, but are not limited to, hydrophilic polymers selected from polyethylene glycols (PEGs), polyvinylpyrrolidones (PVP), hydroxypropyl methylcellulose (HPMC) and poloxamers; UV stabilizers such as benzophenone-3; antioxidants such as tocopheryl acetate; preservatives such as phenoxyethanol, benzyl alcohol, methyl paraben, propyl paraben; pH adjusting agents such as lactic acid, citric acid, sodium citrate, succinic acid, phosphoric acid, sodium hydroxide, sodium carbonate; deodorants and anti-microbials, such as farnesol, zinc phenolsulphonate, and ethylhexylglycerin; humectants such as tribehenin, glycerine; skin conditioning agents such as allantoin; cooling agents such as trimethyl isopropyl butanamide and menthol; hair conditioning ingredients such as panthenol, panthetine, pantotheine, panthenyl ethyl ether, and combinations thereof; propellants such as propane, isopropane, butane, and isobutene; salts in general, such as potassium acetate and sodium chloride and mixtures thereof; perfumes and dyes.

If present, these additional ingredients will preferably be present at a level of less than 10%, more preferably of less than 5%, by weight with respect to the total weight of the composition.

The following examples serve to illustrate the invention without however restricting it.

EXAMPLE 1

Several mixtures of α, β, and γ-cyclodextrins were analysed by sniff test to evaluate their ability to mask body malodour. The composition of the cyclodextrin mixtures are reported in the following Table 1.

TABLE 1

| Sample | % α-cyclodextrin | % β-cyclodextrin | % γ-cyclodextrin |
|---|---|---|---|
| DEO1 | 1.50 | 0.75 | 0.75 |
| DEO2 | 0.75 | 1.50 | 0.75 |
| DEO3 | 0.75 | 0.75 | 1.50 |
| DEO4 | 1.00 | 1.50 | 0.50 |

A blend of malodour compounds, named CFM13668, simulating the component of body sweat which produces malodour, was obtained from CFF S.p.A., Opera, Italy (www.creative-flavours-fragrances.com). The CFM13668 basic sweat contained the malodour compounds as reported in the following Table 2.

TABLE 2

| CAS Number | Compound |
|---|---|
| 101-94-0 | p-cresyl phenylacetate |
| 120-72-9 | indol |
| 103-82-2 | phenylacetic acid |
| 55066-56-3 | p-cresyl isovalerate |
| 68-11-1 | thioglycolic acid |
| 107-92-6 | N-butyric acid |
| 142-62-1 | caproic acid |
| 25265-71-8 | dipropylene glycol |
| 590-86-3 | isovaleraldehyde |
| 503-74-2 | isovaleric acid |

Four specific sweats, simulating a life period and a sexual gender, were prepared by adding to the "basic sweat" two compounds specific for a life cycle or sexual gender, as reported in the following Table 3.

TABLE 3

|  | Sweat A Teenager | Sweat B Woman | Sweat C Man | Sweat D Elderly |
|---|---|---|---|---|
| Testosterone | 250 pmoli/L | — | — | — |
| Dihydrotestosterone | 150-200 pmoli/L | — | — | — |
| 3-methyl-2-hexanoic acid | — | 7-10 µg/L | 7-10 µg/L | — |
| Androstenol | — | 100-150 pmoli/L | — | — |
| Androsterone | — | — | 100-150 pmoli/L | — |
| 2-nonenal | — | — | — | 0.2-0.4% |
| nonanal | — | — | — | 0.2-0.4% |

Five drops of the basic sweat were added to 400 mL of a NaCl 0.9% physiological solution, diluted 1:3 with distilled water. This mixture was used as reference for the sniff test.

Five drops of each Sweat A to D and five drops of each DEO 1 to 4 were added to 400 mL of a NaCl 0.9% physiological solution, diluted 1:3 with distilled water. Sixteen solutions were obtained, each having a volume of about 400 ml and containing a specific Sweat (A to D) in combination with a specific DEO (1 to 4).

All the mixtures were stirred for 5 minutes. The pH was adjusted to 5.5. Aliquots of 2 mL of each mixture were transferred to Pyrex tubes and sealed with sealing plugs.

A sniff test was performed by 8 trained judges after 1, 4 and 8 hours. The judges evaluated the intensity of malodour according to a grading scale, reported in Table 4, where the reference had a score of 5.

TABLE 4

| Grade | Malodour intensity |
|---|---|
| 1 | Much lower than the reference |
| 2 | Lower than the reference |
| 3 | Moderately lower than the reference |
| 4 | Slightly lower than the reference |
| 5 | Equal to reference |
| 6 | Slightly higher than the reference |
| 7 | Moderately higher than the reference |
| 8 | Higher than the reference |
| 9 | Much higher than the reference |

Figure 1:
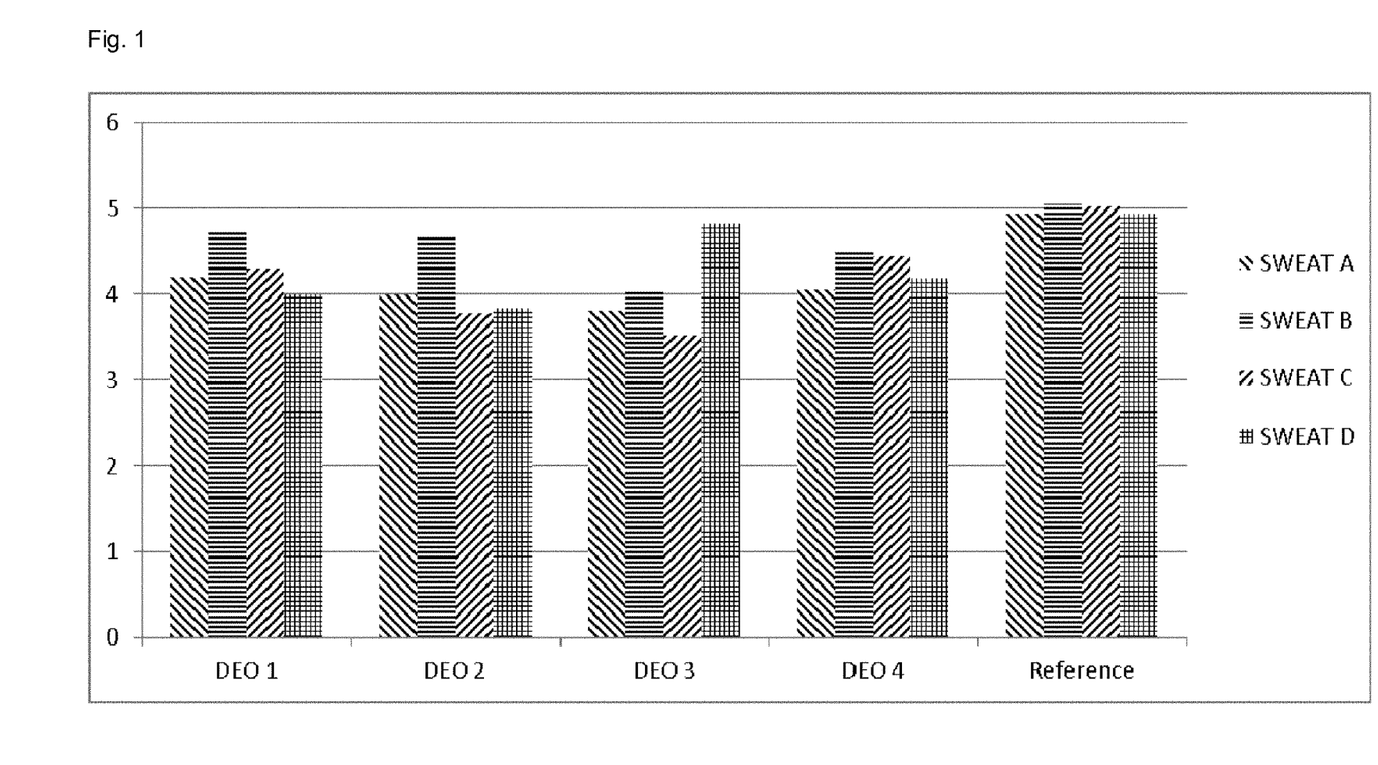
FIG. 1 represents a bar chart comparing the evaluations of the sniff test after 1 hour.
Figure 2:
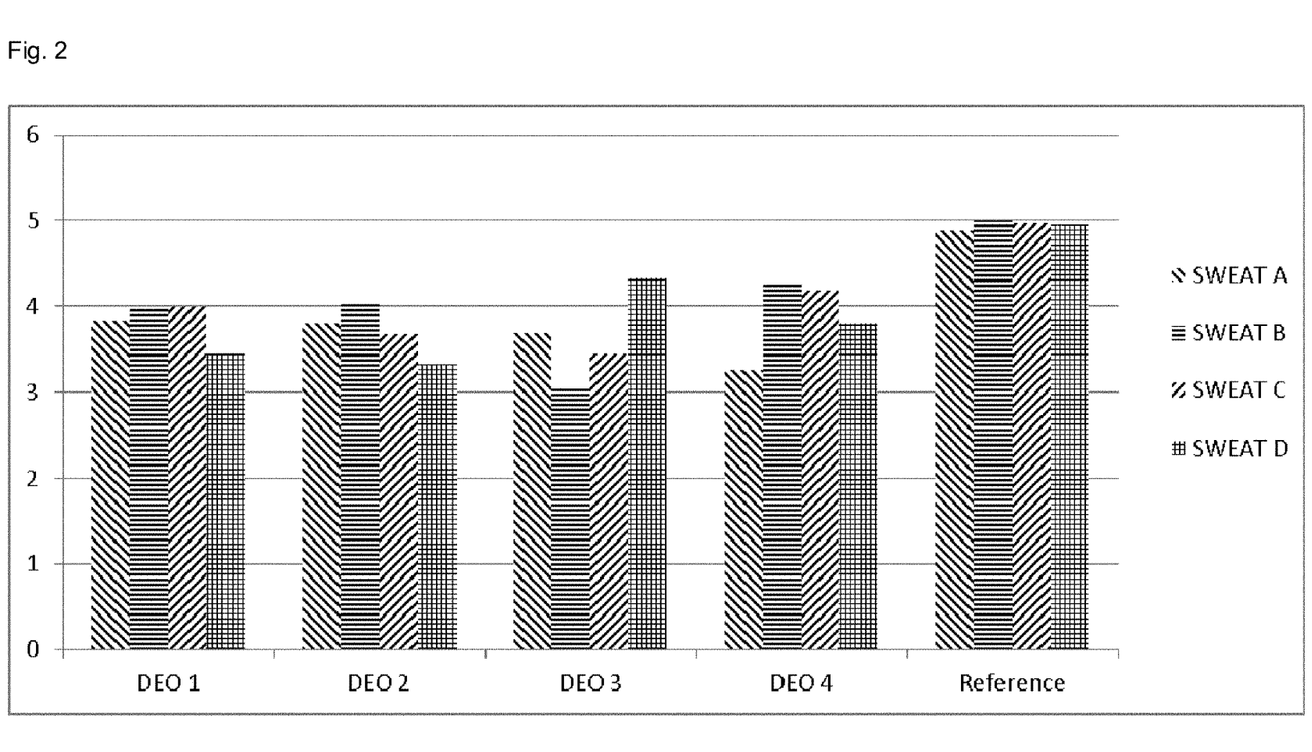
FIG. 2 represents a bar chart comparing the evaluations of the sniff test after 4 hour.
Figure 3:
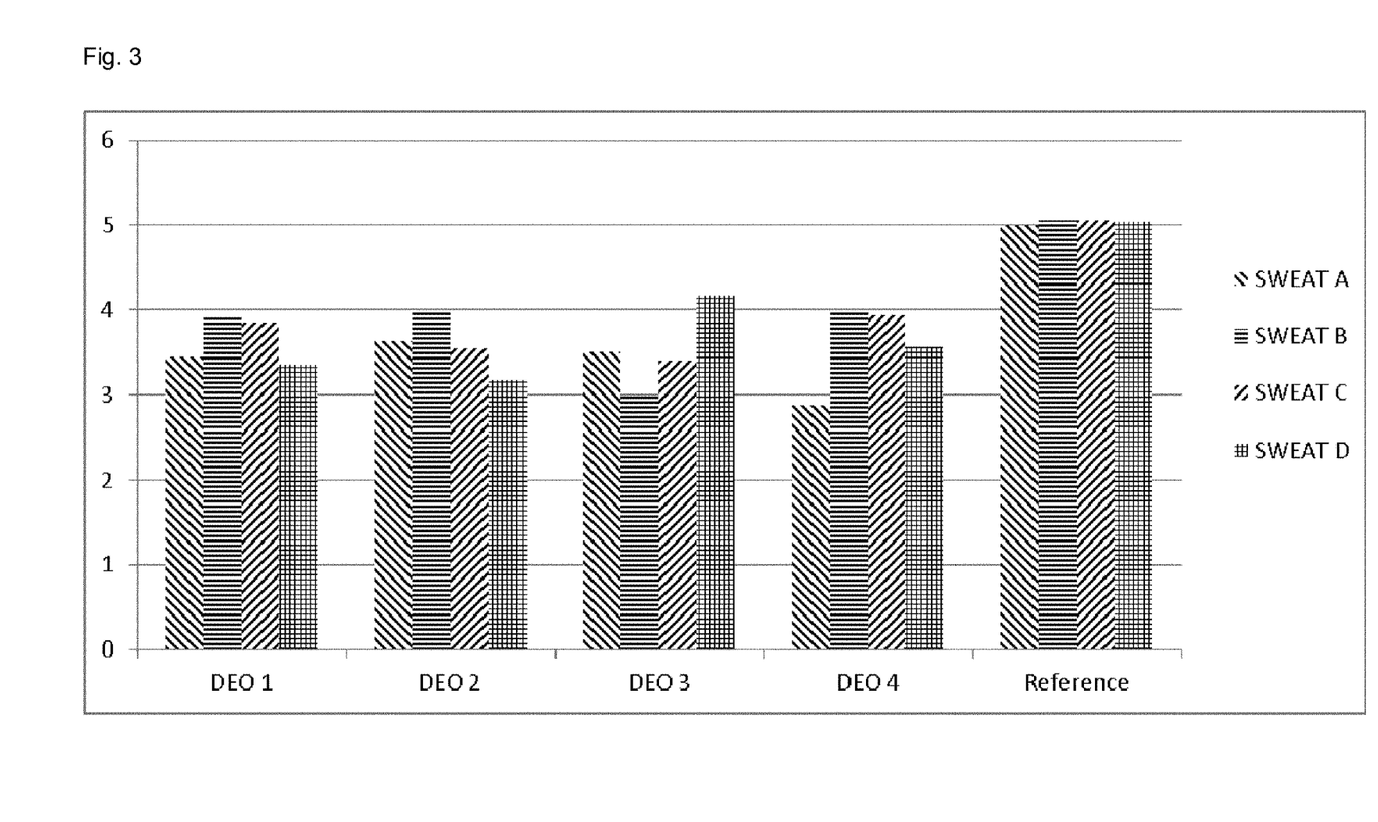
FIG. 3 represents a bar chart comparing the evaluations of the sniff test after 8 hour.

The results of the sniff tests after 1, 4 and 8 hours have been reported in the following Tables 5 to 7, and graphically represented in the attached FIGS. 1 to 3.

TABLE 5

SNIFF TEST AFTER 1 HOUR

| | SWEAT A | SD | SWEAT B | SD | SWEAT C | SD | SWEAT D | SD |
|---|---|---|---|---|---|---|---|---|
| DEO 1 | 4.20 | 0.21 | 4.75 | 0.17 | 4.30 | 0.25 | 4.00 | 0.18 |
| DEO 2 | 4.00 | 0.13 | 4.69 | 0.12 | 3.78 | 0.19 | 3.83 | 0.23 |
| DEO 3 | 3.81 | 0.18 | 4.06 | 0.16 | 3.51 | 0.23 | 4.83 | 0.18 |
| DEO 4 | 4.06 | 0.11 | 4.50 | 0.13 | 4.44 | 0.20 | 4.19 | 0.13 |
| Reference | 4.94 | 0.14 | 5.06 | 0.11 | 5.02 | 0.12 | 4.94 | 0.09 |

SD: Standard Deviation

TABLE 6

SNIFF TEST AFTER 4 HOUR

| | SWEAT A | SD | SWEAT B | SD | SWEAT C | SD | SWEAT D | SD |
|---|---|---|---|---|---|---|---|---|
| DEO 1 | 3.83 | 0.15 | 4.00 | 0.15 | 4.00 | 0.18 | 3.44 | 0.17 |
| DEO 2 | 3.81 | 0.11 | 4.06 | 0.21 | 3.67 | 0.22 | 3.33 | 0.21 |
| DEO 3 | 3.69 | 0.23 | 3.06 | 0.11 | 3.45 | 0.16 | 4.33 | 0.26 |
| DEO 4 | 3.25 | 0.15 | 4.25 | 0.17 | 4.19 | 0.20 | 3.81 | 0.16 |
| Reference | 4.88 | 0.12 | 5.00 | 0.09 | 4.97 | 0.23 | 4.96 | 0.08 |

SD: Standard Deviation

TABLE 7

SNIFF TEST AFTER 8 HOUR

| | SWEAT A | SD | SWEAT B | SD | SWEAT C | SD | SWEAT D | SD |
|---|---|---|---|---|---|---|---|---|
| DEO 1 | 3.45 | 0.22 | 3.94 | 0.14 | 3.85 | 0.19 | 3.35 | 0.18 |
| DEO 2 | 3.63 | 0.13 | 4.00 | 0.15 | 3.55 | 0.23 | 3.17 | 0.19 |
| DEO 3 | 3.50 | 0.15 | 3.00 | 0.13 | 3.40 | 0.25 | 4.17 | 0.20 |
| DEO 4 | 2.88 | 0.11 | 4.00 | 0.09 | 3.94 | 0.06 | 3.56 | 0.12 |
| Reference | 5.00 | 0.16 | 5.06 | 0.11 | 5.05 | 0.20 | 5.04 | 0.12 |

SD: Standard Deviation

The results of Tables 5 to 7 have clearly demonstrated the better efficacy of DEO 4 in masking the malodour of teenagers (Sweat A) compared to the efficacy in masking the malodour of elderly people and adult people (Sweats B-D).

Further, the results of Tables 5 to 7 have clearly demonstrated the better efficacy of DEO 3 in masking the malodour of women (Sweat B) compared to the efficacy in masking the malodour of teenagers, men and elderly people (Sweats A and C-D).

The efficacy of DEO 2 was demonstrated comparable to that of DEO3 in masking the malodour of men (Sweat C), even if the results of Table 5 to 7 are slightly inferior.

Similarly, the efficacy of DEO 1 was demonstrated comparable to that of DEO 2 in masking the malodour of elderly people (Sweat D), even if the results of Table 5 to 7 are slightly inferior.

EXAMPLE 2

The following Tables 8 to 17 provide several examples of preferred embodiment of odour-absorbing compositions according to the present invention. All compositions can be preferably realized with a weight ratio of α-, β-, and γ-cyclodextrins of 1:1.5:0.5 when intended for teenagers, 1:1:2 when intended for women, 1:1:2 or, preferably, 1:2:1 when intended for men, and 1:2:1 or, preferably, 2:1:1 when intended for elderly people.

TABLE 8

Cream deodorant 1

| Ingredients | Range % |
|---|---|
| Water | from 50 to 80% |
| Aluminum chlorohydrate | from 0 to 20% |
| Cetearyl alcohol | from 2 to 5% |
| α-, β-, and γ-cyclodextrins | from 0 to 5% |
| Cetyl alcohol | from 1 to 3% |
| Dimethicone | from 1 to 3% |
| Caprylyl methicone | from 1 to 3% |

TABLE 8-continued

Cream deodorant 1

| Ingredients | Range % |
| --- | --- |
| Cyclopentasiloxane | from 1 to 3% |
| Parfum | from 0.5 to 2% |
| Ceteareth-20 | from 0 to 1% |
| Polysilicone-11 | from 0 to 1% |
| 2-Methyl 5-cyclohexylpentanol | less than 1% |
| Guar hydroxypropyltrimonium chloride | less than 1% |
| Cetrimonium chloride | less than 1% |
| Sodium hydroxide | less than 1% |

TABLE 9

Cream deodorant 2

| Ingredients | Range % |
| --- | --- |
| Cyclopentasiloxane | from 53 to 64% |
| Aluminum zirconium tetrachlorohydrex gly | from 16 to 30% |
| Dimethicone | from 3 to 8% |
| Tribehenin | from 3 to 8% |
| α-, β-, and γ-cyclodextrins | from 0 to 5% |
| Water | from 1 to 3% |
| C18-36 acid triglyceride | from 1 to 2% |
| Parfum | from 0.5 to 2% |
| Panthenyl triacetate | less than 2% |
| Tocopheryl acetate | less than 1% |
| Parfum | less than 1% |

TABLE 10

Roll-on deodorant 1

| Ingredients | Range % |
| --- | --- |
| Water | from 40 to 60% |
| Aluminum chlorohydrate | from 0 to 30% |
| Ethylhexyl stearate | from 1 to 8% |
| PPG-15 stearyl ether | from 0 to 5% |
| α-, β-, and γ-cyclodextrins | from 0 to 5% |
| Ceteareth-25 | from 1 to 3% |
| Glyceryl stearate | from 1 to 3% |
| Stearoxy dimethicone | from 1 to 3% |
| Dimethicone | from 1 to 3% |
| Glycerin | from 0 to 3% |
| Parfum | from 0.5 to 2% |
| Triethyl citrate | from 0 to 2% |
| Phenoxyethanol | from 0 to 1% |
| Stearyl Alcohol | less than 1% |

TABLE 11

Roll-on deodorant 2

| Ingredients | Range % |
| --- | --- |
| Water | from 55 to 85% |
| Aluminum chlorohydrate | from 0 to 30% |
| PPG-15 stearyl ether | from 1 to 5% |
| Steareth-2 | from 1 to 3% |
| Steareth-20 | from 1 to 3% |
| Parfum | from 0.5 to 2% |
| Isohexadecane | from 0 to 2% |
| Dipropylene Glycol | from 0 to 2% |
| Glycerin | from 0 to 2% |
| Triethyl citrate | from 0 to 2% |
| Zinc Phenolsulfonate | from 0 to 1% |
| Phenoxyethanol | less than 1% |
| 2-Methyl 5-cyclohexylpentanol | less than 1% |
| Decylene glycol | less than 1% |
| α-, β-, and γ-cyclodextrins | from 0 to 5% |

TABLE 12

Spray deodorant 1

| Ingredients | Range % |
| --- | --- |
| Butane | from 30 to 65% |
| Isobutane | from 12 to 23% |
| Propane | from 11 to 21% |
| Cyclopentasiloxane | from 5 to 25% |
| Aluminum chlorohydrate | from 0 to 8% |
| α-, β-, and γ-cyclodextrins | from 0 to 5% |
| Dimethicone | less than 2% |
| Parfum | from 0.5 to 2% |
| Disteardimonium hectorite | less than 2% |
| Triethyl citrate | from 0 to 2% |
| Phenoxyethanol | from 0 to 1% |
| 2-Methyl 5-cyclohexylpentanol | from 0 to 1% |
| Ethylhexylglycerin | from 0 to 1% |
| Water | from 0 to 1% |

TABLE 13

Spray deodorant 2

| Ingredients | Range % |
| --- | --- |
| Butane | from 35 to 65% |
| Isobutane | from 13 to 25% |
| Propane | from 12 to 22% |
| Water | from 4 to 11% |
| Aluminum chlorohydrate | from 2 to 5% |
| α-, β-, and γ-cyclodextrins | from 0 to 5% |
| Cyclopentasiloxane | from 1 to 4% |
| Parfum | from 0.5 to 2% |
| C12-13 alkyl lactate | less than 1% |
| PEG/PPG-18/18 dimethicone | less than 1% |
| Caprylyl glycol | less than 1% |
| Ethyl hexylglycerin | less than 1% |

TABLE 14

Stick deodorant 1

| Ingredients | Range % |
| --- | --- |
| Cyclopentasiloxane | from 23 to 42% |
| Stearyl alcohol | from 11 to 21% |
| Aluminum chlorohydrate | from 10 to 18% |
| C12-15 alkyl benzoate | from 5 to 15% |
| PPG-14 butyl ether | from 3 to 9% |
| Talc | from 3 to 9% |
| Hydrogenated castor oil | from 2 to 7% |
| α-, β-, and γ-cyclodextrins | from 0 to 5% |
| Paraffinum liquidum | from 2 to 5% |
| Petrolatum | from 2 to 5% |
| Parfum | from 0.5 to 2% |
| Water | less than 1% |
| Behenyl alcohol | less than 1% |

TABLE 15

Stick deodorant 2

| Ingredients | Range % |
| --- | --- |
| Dipropylene glycol | from 25 to 50% |
| Water | from 15 to 35% |
| PEG-200 | from 14 to 26% |
| Glycerin | from 5 to 15% |
| Sodium stearate | from 3 to 8% |
| α-, β-, and γ-cyclodextrins | from 0 to 5% |
| Parfum | from 0.5 to 2% |
| PPG-3 myristyl ether | less than 2% |
| Isopropyl myristate | less than 1% |

TABLE 15-continued

Stick deodorant 2

| Ingredients | Range % |
| --- | --- |
| BHT | less than 1% |
| Sodium hydroxide | less than 1% |

TABLE 16

Deo vapo 1

| Ingredients | Range % |
| --- | --- |
| Alcohol denaturated | from 28 to 52% |
| Cyclopentasiloxane | from 19 to 36% |
| PPG-3 myristyl ether | from 11 to 20% |
| C12-15 alkyl benzoate | from 5 to 14% |
| Water | from 2 to 5% |
| α-, β-, and γ-cyclodextrins | from 0 to 5% |
| Parfum | from 0.5 to 3% |
| Dimethicone | less than 2% |
| Zinc phenolsulfonate | less than 2% |

TABLE 17

Deo vapo 2

| Ingredients | Range % |
| --- | --- |
| Water | from 79 to 97% |
| PEG-40 hydrogenated castor oil | from 2 to 5% |
| α-, β-, and γ-cyclodextrins | from 0 to 5% |
| Dipropylene glycol | from 1 to 3% |
| Ceteareth-20 | from 1 to 2% |
| Parfum | from 0.5 to 2% |
| Triethyl citrate | less than 2% |
| Glycerin | less than 2% |
| Phenoxyethanol | less than 1% |
| 2-Methyl 5-cyclohexylpentanol | less than 1% |

TABLE 17-continued

Deo vapo 2

| Ingredients | Range % |
| --- | --- |
| Ethylhexylglycerin | less than 1% |
| Propylene glycol | less than 1% |
| Decylene glycol | less than 1% |
| Dicaprylyl ether | less than 1% |

The invention claimed is:

1. An odor-absorbing composition comprising a mixture of α-, β-, and γ-cyclodextrins, wherein the amount of one of said α-, β-, and γ-cyclodextrins is equal to or higher than the total amount of the other two cyclodextrins,
    wherein the weight ratio of the amount of said β-cyclodextrins to the amount of said α-, and γ-cyclodextrins ranges from 4:1 to 1:1.

2. The odor-absorbing composition according to claim 1, wherein said composition comprises an amount of said α-, β-, and γ-cyclodextrins in a weight ratio of about 1:2:1.

3. The odor-absorbing composition according to claim 1, wherein the amount of said α-cyclodextrins is higher than the amount of said γ-cyclodextrins.

4. The odor-absorbing composition according to claim 3, wherein the the weight ratio of the amount of said α-cyclodextrins to said γ-cyclodextrins ranges from 4:1 to 1.5:1.

5. The odor-absorbing composition according to claim 4, wherein the weight ratio of the amount of said β-cyclodextrins to the amount of said α-, and γ-cyclodextrins ranges from 2:1 to 1:1.

6. The odor-absorbing composition according to claim 3, wherein said composition comprises an amount of said α-, β-, and γ-cyclodextrins in a weight ratio of about: 1:1.5:0.5.

7. The odor-absorbing composition according to claim 1, wherein the weight ratio of the amount of said β-cyclodextrins to the amount of said α-, and γ-cyclodextrins ranges from 2:1 to 1:1.

* * * * *